US00PP13709P29

(12) United States Plant Patent
Vardi et al.

(10) Patent No.: US PP13,709 P2
(45) Date of Patent: Apr. 1, 2003

(54) CITRUS TREE NAMED 'TAMI'

(75) Inventors: Aliza Vardi, Ramat Gan (IL); Pinchas Spiegel-Roy, Ramat-Gan (IL); Ahuva Frydman-Shani, Ramat-Gan (IL); Avraham Elchanati, Holon (IL); Hana Neumann, Hemed (IL)

(73) Assignee: State of Israel-Ministry of Agriculture and Rural Development, Tel Aviv (IL)

( * ) Notice: Subject to any disclaimer, the term of this patent is extended or adjusted under 35 U.S.C. 154(b) by 0 days.

(21) Appl. No.: 09/718,471

(22) Filed: Nov. 20, 2000

(51) Int. Cl.[7] ..... A01H 5/00
(52) U.S. Cl. ..... Plt./202

(58) Field of Search ..... Plt./202

(56) References Cited

PUBLICATIONS

GTITM UPOVROM Citation for 'Tami' as per IL PBR 02639; Feb. 26, 1999.*

* cited by examiner

*Primary Examiner*—Kent Bell
(74) *Attorney, Agent, or Firm*—Akerman Senterfitt

(57) ABSTRACT

A new variety of mandarin citrus is described that is distinguished by having seedless fruit and occasionally fruit with a few seeds, an early ripening period, and fruit which is orange when fully ripe.

2 Drawing Sheets

FIELD OF THE INVENTION

A new mandarin citrus tree *Citrus reticulata* hydrid is described. The new variety named 'Tami' is desirable to the consumer because of the flavor and orange color of its fruit and to the commercial grower because of its early-season fruit ripening.

BACKGROUND OF THE NEW PLANT

The present invention relates to a new and distinct variety of mandarin citrus tree *Citrus reticulata* hybrid developed by inventors Aliza Vardi, Pinchas Spiegel-Roy, Avraham Elchanati, Ahuva Frydman-Shani and Hana Neumann in Bet Dagan, Israel from a controlled pollination cross between seed bearing parent 'Temple' tangor (unpatented) and pollen parent 'Michal' (unpatented) mandarin.

Asexual reproduction by conventional bud grafting of the new variety at the Agriculture Research Organization Volcani Center in Bet Dagan, Israel, has shown that the new characteristics are stabilized and permanently fixed through successive propagation.

The objective in breeding the present new tree variety, assigned the denomination 'Tami', was to obtain early ripening seedless mandarin citrus. In the spring of 1980, the seed parent 'Temple' tangor was crossed with pollen parent 'Michal' mandarin, a cultivar of Israeli origin believed to be a natural hybrid between two *Citrus reticulata* Blanco cultivars. The fruit was collected in November 1980. Seeds were extracted and germinated in January 1981. About 60 seedlings were grafted onto Troyer rootstock during September 1981. The grafted plants were planted in an experimental grove in the Volcani Center, Bet Dagan, in June 1982.

The first fruits were observed in November 1985 and again in 1986. One of the 60 scions was selected and numbered 2/65. At the beginning of October, the fruit of this selection was light green-orange and was seedless except that several fruits had a few seeds (1–6) per fruit. At the last week in October the fruit was orange in color and in November was fully ripe.

Bud wood was taken from 2/65 and grafted in the spring of 1987 on 10 Troyer rootstocks. The grafted plants were planted in the experimental grove of the Agricultural Research Organization, Bet Dagan, Israel. The first crop of these trees was obtained in 1991. The yield was good and the fruit had an excellent flavor.

SUMMARY OF THE INVENTION

2/65, designated 'Tami', is characterized by early fruit ripening of seedless fruit. Occasionally fruit may contain a few seeds when cross-pollinated. Fruit is orange in color when fully ripe. Table 1 shows some of the characteristics of 'Tami' compared with the seed parent 'Temple' tangor and pollen parent 'Michal'.

TABLE 1

| Tree | Shape of fruit | Size of fruit | Seeds/fruit | Rind |
|---|---|---|---|---|
| 2/65 'Tami' | Oblate | Medium | 0–6 | Thin, yellow-orange, RHS 23B |
| 'Temple' tangor | Broadly oblate to slightly subglobose, short wrinkled or furrowed neck | Medium large | 15–20 | Pebbled, medium thick, red-orange |
| 'Michal' | Slightly oblate to globose with small navel | Variable-small to medium | 2–9 | Smooth, deep orange-red RHS 33A |

The following is a detailed description of the new mandarin citrus variety based on observations made under typical Israeli grove conditions.

The tree is small to medium sized, up to 2 meters in height and about 3 meters wide at 6–7 years after planting. The tree has small thorns only at the juvenile stage; at the productive stage it is thornless.

The chromosome number of the tree is diploid (2n=18) as is the chromosome number of 'Temple' and 'Michal'. The foliar canopy is less dense than that of Temple or 'Michal'. The color of the bark of the older parts of the tree is yellow-green. The tree is probably self-incompatible and quite productive with a very slight tendency to alternate bearing (lower yield of fruit after a year of heavy bearing if not picked). The fruit bearing buds are thornless. Young shoots have no anthocyanin coloration in the tip.

Foliar flushes, as measured in Bet Dagan, Israel, occur between April and September. The color and veination of the leaves are similar to that of 'Michal' and 'Temple'. The leaves are somewhat variable; medium to small, lanceolate or lanceolate and sharp pointed. Leaf blades are firm, without undulation and straight in cross section. Petioles are without wings or have rudimentary wings.

Flowering, as measured in Bet Dagan, Israel, is between mid March and mid April, depending on the climate conditions. Terminal flower buds have no anthocyanin coloration. Flowers are borne singly. Anther color is yellow with viable pollen present and trees flower once per year.

Fruit ripening as measured in Bet Dagan, Israel, is from October to November The majority of the fruits are seedless, but occasionally the fruit has about 1–6 seeds even when optimal pollination conditions are employed. The fruit shape is oblate and it is medium sized. When 50 fruits were measured, the fruit had an average weight of 95 grams, an average height of 51 mm, and an average diameter of 59 mm. The fruit surface is usually smooth with a yellow orange color, 23B, on The Royal Horticultural Society of London Colour Chart, and bears an average number of conspicuous rind oil glands. Fruit ripening does not differ from outside of the canopy to the inside, but the fruit color of the outside canopy is a little brighter as compared to the fruit color of the inside canopy. A style does not persist and a navel is absent or very rare. The rind is thin and easy to peel.

The above fruit characteristics differ from both 'Temple' and 'Michal'. 'Temple' has a medium-large fruit, a very broadly oblate to slightly subglobose shape, sometimes with a short wrinkled or furrowed neck and medium thick, moderately adherent but readily peelable rind with a deep reddish-orange color and a somewhat pebbled or rough surface. 'Michal' has fruits of variable size ranging from small to medium, a slightly oblate to globose shape, occasionally with a small navel and a smooth, easy peeled rind with a deep reddish-orange color.

The color of the albedo is white and the flesh is orange. The fruit contains 9–11 segments and is very juicy. The external color of the seeds when present is greyed green when fresh. The internal seed coat is greyed green. The cotyledons are green.

The seeds when present are smooth and polyembryonic with few embryos as are the seeds of the pollen parent Michal. This is in contrast to the seeds of 'Temple' which are monoembryonic. The ripening of the fruit on the tree and within the fruit is uniform. Fruit remaining on the tree does not regreen and does begin to lose quality until the end of November.

DESCRIPTION OF THE PHOTOGRAPHS

The new citrus tree is illustrated in the accompanying color photographs.

Sheet one depicts the whole tree and canopy shape of the new variety.

Sheet two shows the exterior of the fruit as well as transverse midsections in a plane substantially perpendicular to the axis, illustrating the seedless interior of one fruit half and a single seed in the other half.

DESCRIPTION OF THE NEW TREE

The following is a detailed description of the new mandarin citrus variety 'Tami' based on observations made under typical Israeli grove conditions. Color designations have been determined from The R.H.S. Colour Chart published by The Royal Horticultural Society, London. Observations were made on trees 4–5 years of age.

Tree:

*Origin.*—Cross between seed parent 'Temple' tangor and pollen parent 'Michal'.

*Classification.*—Botanical: *Citrus reticulata* hybrid. Common: Mandarin citrus. Cultivar: 'Tami'.

*Shape.*—Somewhat bushy, about 3 m wide, 2 m height.

*Thorns.*—Small thorns at the juvenile stage; productive stage is thornless.

*Branching.*—Upright.

*Canopy.*—Low, moderately dense.

*Bark.*—Immature: RHS 137C. Mature: Yellow-green, RHS 148B.

*Height.*—2 m (6–7 years).

*Width.*—3 m (6–7 years).

*Productivity.*—50 kg per tree per season at age 7.

*Leaf.*—Lanceolate. Size: 75 mm length, 32 mm width. Shape: Lanceolate, tapering apex. Leaf blade: Firm, without undulation, cross section straight. Petioles: Wingless, 8 mm length, 1.7 mm in diameter, Green RHS 147B. Color: Upper: Green RHS 147A; lower: Green RHS 147B. Foliar flushes: April–September.

*Habit.*—Medium vigorous.

*Disease resistance.*—No particular susceptibility or resistance observed.

*Trunk diameter (20 cm above the ground).*—31 cm.

*Winter hardiness.*—Winter temperature in Bet Dagan, Israel averages 4–7 degrees Centigrade.

Flower:

*Petals.*—5.

*Petal color.*—White RHS 155B.

*Flowering period.*—Mid March to mid April (Israel).

*Flower drop.*—April.

*Stamens.*—20.

*Anther color.*—Yellow RHS 11B.

*Pollen fertility.*—Fertile.

*Anthocyanin coloration.*—No coloration.

Fruit:

*Shape.*—Oblate.

*Size.*—Height: 51 mm, Diameter 59 mm.

*Weight.*—95 g (average of 50 fruits).

*Surface color.*—Yellow-orange RHS 23B.

*Rind oil gland.*—Conspicuous, about 35/cm$^2$.

*Style.*—No persistence.

*Navel.*—Absent.

*Rind.*—3 mm thick, easy to peel. Texture: smooth. Aroma: typical citrus orange peel.

*Albedo.*—White RHS 155B.

*Areola.*—Incompletely developed.

*Fruit segments.*—9–11.

*Color of flesh.*—Yellow-orange RHS 23B. Time to maturity: October to November (Israel). Time of picking: October to November (Israel).

*Fruit extract.*—(Quality tested Oct. 29, 1994). Total soluble solids (TSS): 13.5%. Acid content: 1.1%. TSS/acid ratio: 9.0. Taste: Pleasant.

Seeds:

*Number per fruit.*—Majority of the fruit are seedless: occasionally 1–6 seeds per fruit.

*Size.*—Length: 10 mm, Width: 6 mm.

*Color.*—External: Greyed-green RHS 193C. Internal: Greyed-green, 199D.

*Cotyledons.*—Green, RHS 142C.

*Embryony.*—Polyembryonic.

The tree and its fruit as described herein may vary somewhat in certain characteristics due to climatic and/or soil conditions under which the variety is grown.

What is claimed is:

1. A new and distinct variety of *Citrus reticulata* hybrid tree substantially as herein described and shown.

* * * * *

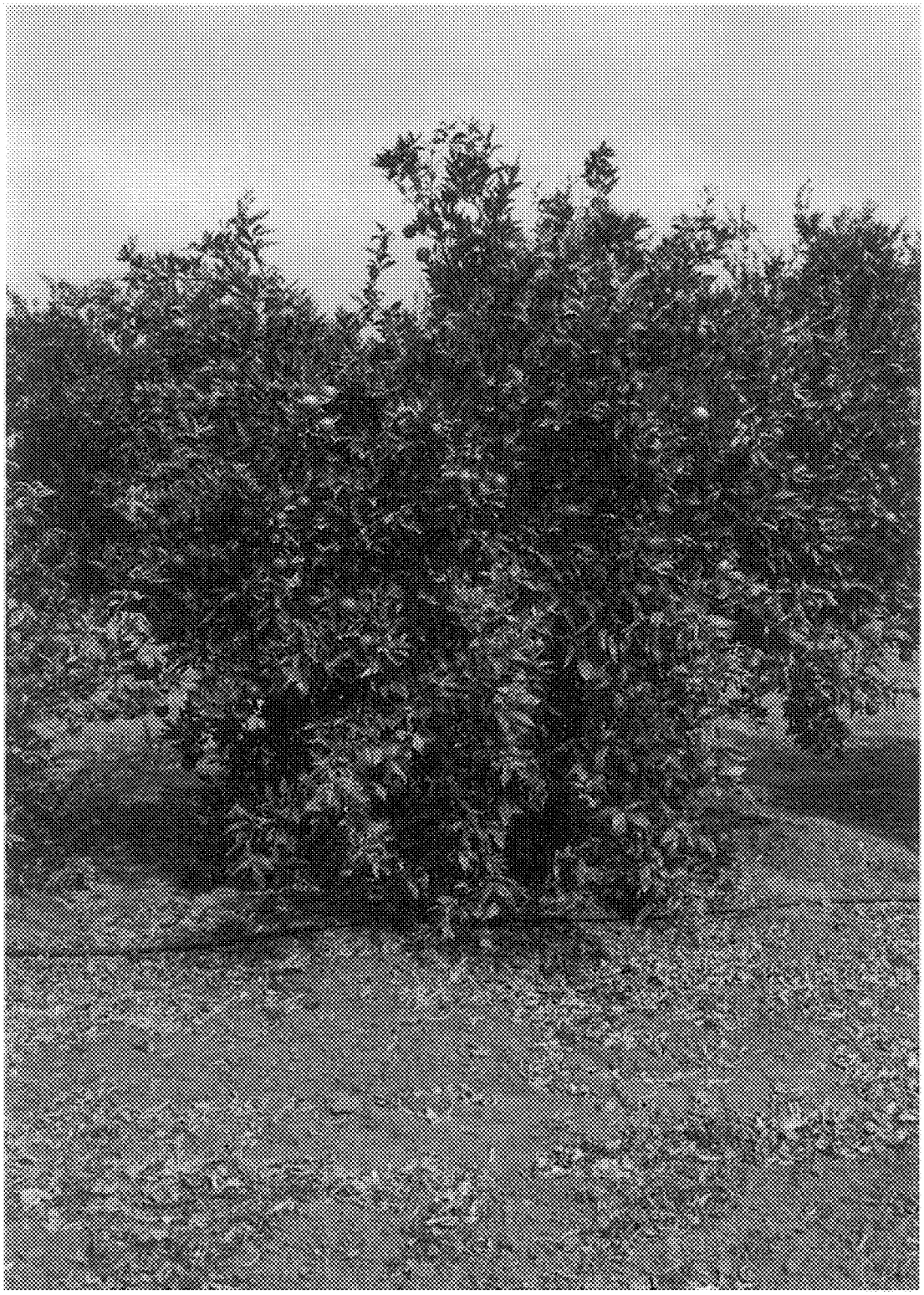

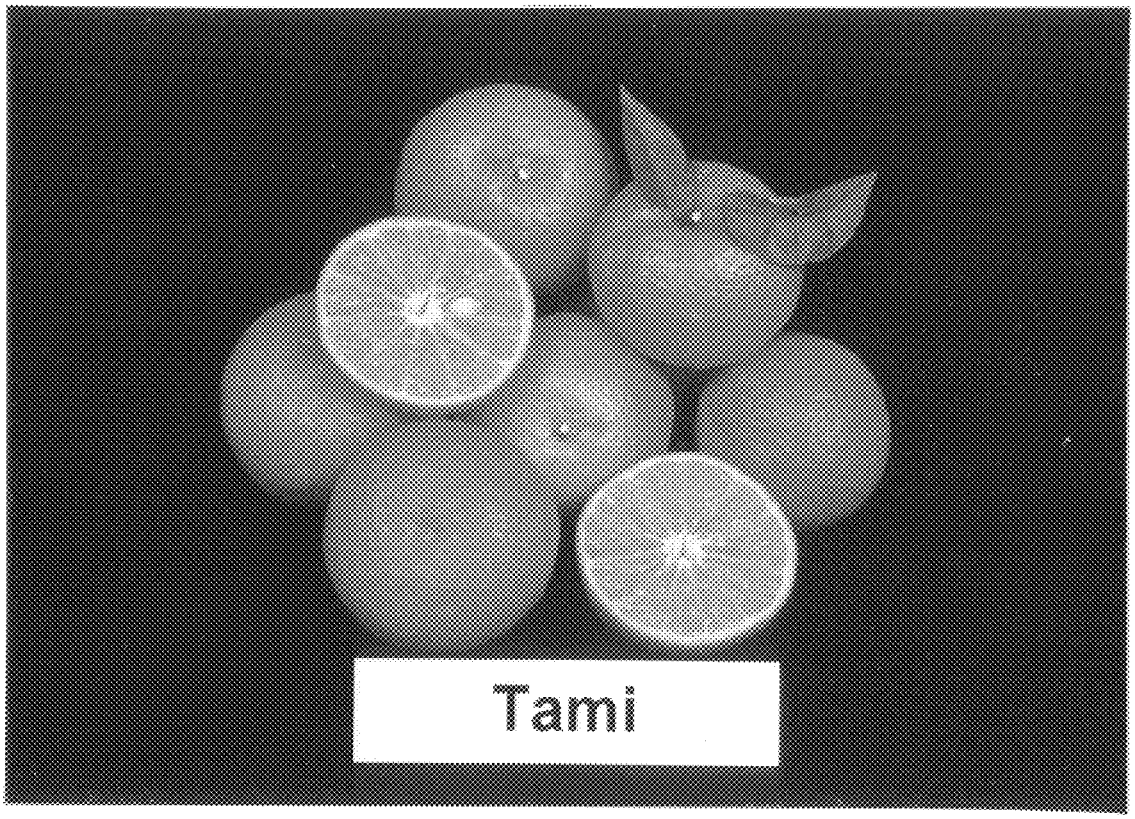
Tami